United States Patent [19]
De Boer et al.

[11] Patent Number: 5,648,261
[45] Date of Patent: Jul. 15, 1997

[54] **STRAINS OF *PHAFFIA RHODOZYMA* CONTAINING HIGH LEVELS OF ASTAXANTHIN AND LOW LEVELS OF 3-HYDROXY-3',4'-DIDEHYDRO-β, Ψ-CAROTEN-4-ONE (HDCO)**

[75] Inventors: Lex De Boer, Wateringen; Bart Van Hell, Delft; Andreas Jacobus Johanna Krouwer, Poeldijk, all of Netherlands

[73] Assignee: Gist-brocades, N.V., Ma Delft, Netherlands

[21] Appl. No.: 107,811

[22] PCT Filed: Dec. 17, 1992

[86] PCT No.: PCT/NL92/00231

§ 371 Date: Oct. 12, 1993

§ 102(e) Date: Oct. 12, 1993

[87] PCT Pub. No.: WO93/12249

PCT Pub. Date: Jun. 24, 1993

[30] Foreign Application Priority Data

Dec. 17, 1991 [EP] European Pat. Off. ............. 91203312

[51] Int. Cl.$^6$ .............................. C12N 1/16; C12P 23/00
[52] U.S. Cl. ..................... 435/254.2; 435/255.1; 435/172.1; 435/67
[58] Field of Search ............................ 435/67, 255.1, 435/172.1, 254.2

[56] References Cited

U.S. PATENT DOCUMENTS

| 5,182,208 | 1/1993 | Johnson et al. | 435/255.1 |
| 5,212,088 | 5/1993 | Prevatt | 435/255.1 |

FOREIGN PATENT DOCUMENTS

| 0427405 | 10/1990 | European Pat. Off. . |
| 0438182 | 1/1991 | European Pat. Off. . |
| 0454024 | 10/1991 | European Pat. Off. . |
| 0482544 | 4/1992 | European Pat. Off. . |
| 8808025 | 10/1988 | WIPO . |

OTHER PUBLICATIONS

An, G–M et al., "Isolation of *Phaffia rhodozyma* Mutants with Increase Astaxanthin Content", *Appl. Enviromental Microbiol.*, vol. 55, No. 1, pp. 116–124 1989.

Lewis et al., "Selection of Astaxanthin–Overproducing Mutants of *Phaffia rhodozyma* with β–Inone", *Appl. Enviromental Microbiol.*, vol. 56, No. 9, 1990.

Jacobson, G.K. "Mutations", In: Biotechnology, vol. 1, Pub. Verlag Chemi; Rehm et al (eds) pp. 296–299, 1981.

Creuger et al (eds), "Strain Development", In: Biotechnology: A Textbook of Industrial Microbiology, Pub: Sinauer Assoc. Inc. pp. 9–58, 1990.

Phaff et al., "A Competitive Study of the Yeast Florae Associated with Trees on the Japanese Islands and on the West Coast of North America" *Proc. IV IFS: Ferment. Technol. Today*, pp. 759–774. Ed. G. Terui, Kyoto (1972).

An and Johnson, "Influence of light on growth and pigmentation of the yeast *Phaffia rhodozyma*", *Antonie van Leeuwenhoek* 57:191–203 (1990).

*Primary Examiner*—Michael G. Wityshyn
*Assistant Examiner*—Francisco C. Prats
*Attorney, Agent, or Firm*—Morrison & Foerster LLP

[57] ABSTRACT

The present invention provides *Phaffia rhodozyma* strains having increased levels of astaxantin and a low percentage of 3-hydroxy-3',4'-didehydro-β,ψ-caroten-4-one (HDCO). Such strains are obtained by a combination of mutagenesis and selection. The invention further provides a method for obtaining such strains. The invention also provides astaxanthin obtained from a mutagenized strain of *Phaffia rhodozyma* characterized in that it contains a decreased relative amount of HDCO.

9 Claims, No Drawings

STRAINS OF *PHAFFIA RHODOZYMA* CONTAINING HIGH LEVELS OF ASTAXANTHIN AND LOW LEVELS OF 3-HYDROXY-3',4'-DIDEHYDRO-β, Ψ-CAROTEN-4-ONE (HDCO)

FIELD OF THE INVENTION

This invention relates to the microbial production of astaxanthin. Specifically, yeast strains are disclosed with a high astaxanthin production level and a low level of 3-hydroxy-3',4'-didehydro-β,ψ-caroten-4-one (HDCO).

BACKGROUND OF THE INVENTION

Astaxanthin is a naturally occurring carotenoid which is responsible for the red colour in salmon, trout, sea bream and other fishes. In natural surroundings this carotenoid is obtained with the feed of these animals in the form of crustaceans and other astaxanthin-containing organisms.

Fish raised on fish-farms or in hatcheries are generally pale and lack the skin and flesh colours of their naturally raised congeners, this is due to a lack of dietary astaxanthin. The addition of astaxanthin to the feed of the fishes is an appropriate way to overcome the colour problem of fish raised in non-natural surroundings.

Astaxanthin applied for this purpose can be obtained by semi-synthetical means. For regulatory reasons and due to increasing pressure excercised by consumers it may be favourable to use astaxanthin from natural sources.

Natural sources of astaxanthin are krill and crawfish shells, algae, flowers and yeast. Astaxanthin extracted from krill and crawfish is very expensive. The yield of astaxanthin in algae is high but large-scale production of algae is difficult. Therefore attention has turned to the use of yeast, specifically *Phaffia rhodozyma* for the production of astaxanthin.

The astaxanthin-containing yeast *Phaffia rhodozyma* was first isolated in the early 1970s from exudates of deciduous trees in mountainous regions of Japan and Alaska (Phaff et al. (1972) in *Proceedings of the 4th IFS: Fermentation Technology Today*, p. 759–774. Ed. G. Terui, Kyoto). In wild-type *Phaffia rhodozyma* strains astaxanthin concentrations have been determined. Johnson and Lewis ((1979), *J. Gen. Microbiol.* 155 173–183) have found that the concentration of astaxanthin which is dependent on culture conditions varies considerably but never exceeds 650 μg per g yeast dry weight. When growing the yeast under different growth conditions the authors have found, after acetone extraction of the carotenoids, that one of the main contaminants of astaxanthin is 3-hydroxy-3',4'-didehydro-β,ψ-caroten-4-one (HDCO).

Under aerobic conditions the amount of HDCO is about 0.5–1.5% of the amount of astaxanthin. Under microaerophilic conditions this amount increases up to about 26%, (Johnson and Lewis cited above) this amount is too high.

The astaxanthin concentration of about 650 μg/g dry weight as reported for wild type *Phaffia rhodozyma* strains is much too low to make the process economically attractive. Therefore extensive studies have been performed to increase the yield of astaxanthin.

As indicated above Johnson and Lewis (1979) already describe a myriad of different culture conditions (pH, temperature, carbon source, oxygen pressure and light are but a number of factors) which influence the intracellular astaxanthin concentration in Phaffia. A more promising approach for obtaining higher astaxanthin concentrations is classical mutagenesis. An and Johnson ((1990) *Antonie van Leeuwenhoek* 57: 191–203) report that N-methyl-N'-nitro-N-nitrosoguanidine (NTG) mutagenesis of natural *Phaffia rhodozyma* strains gave rise to strains with increased carotenoid contents, amounts of up to 1050 μg/g dry weight are reported.

The strains grown under different conditions described by An and Johnson (opt.cited) were found to contain from 10–15% of total carotenoids in the form of HDCO (about 30% of the amount of astaxanthin). Also Lewis et al ((1990) *Appl. Environm. Microbiol.* 56: 2944–2945) have shown that the amount of HDCO as compared to astaxanthin increases due to mutagenesis. In their situation (Table 1) HDCO increased from 4 to 8%.

No biological effects of HDCO are known. In fact till now HDCO has only been reported in *Phaffia rhodozyma*. High amounts of HDCO which seem to be increasing due to mutagenesis are unacceptable as additions to animal feed.

Therefore there is clearly a need for astaxanthin obtained from Phaffia which has a low HDCO content. The present invention provides such an astaxanthin.

SUMMARY OF THE INVENTION

The present invention provides *Phaffia rhodozyma* strains having a high astaxanthin content with a low percentage of HDCO.

The present invention also provides astaxanthin obtained from mutagenized *Phaffia rhodozyma* strains having a high astaxanthin content with a low percentage of HDCO.

The present invention further provides a method for obtaining *Phaffia rhodozyma* strains having a high astaxanthin content with a low percentage of HDCO.

In reverse this method can be employed for obtaining a *Phaffia rhodozyma* strain having a decreased level of astaxanthin and a low percentage of HDCO.

DETAILED DESCRIPTION OF THE INVENTION

*Phaffia rhodozyma* CBS 6938 was obtained from the Centraal Bureau voor Schimmelcultures (Baarn, The Netherlands).

In general terms the present invention discloses *Phaffia rhodozyma* strains having a high astaxanthin level and a relatively low percentage of HDCO. Said strains are obtained by a method comprising the following steps;

mutagenizing a *Phaffia rhodozyma* strain, visually selecting a strain with increased colour intensity or visually selecting (intensively) coloured orange colonies with high astaxanthin and low HDCO content compared to the astaxanthin content, from a population of red colonies (with high astaxanthin and a high HDCO content relative to the amount of astaxanthin), growing the selected strain on a fluid medium, extracting the carotenoids from the cells, determining the amounts of carotenoids, selecting a strain with an increased level of astaxanthin and a low level of 3-hydroxy-3',4'-didehydro-β,ψ-caroten -4-one.

Mutagenesis is performed on the *Phaffia rhodozyma* strains in a number of ways for example by UV irradiation, or by treatment with certain mutagenic substances e.g. ethyl methane sulphonate, N-methyl-N'-nitro-N-nitrosoguanidine or other nucleotide base analogues.

Mutated strains are selected on the basis of colour intensity and/or difference in colour and the carotenoids were extracted for example by acetone extraction.

Selection on the basis of colour difference is performed as follows

Appropriate dilutions of a mutagenized cell suspension were plated out on agar plates containing synthetic medium. The dilution was chosen in such a way that 400–450 colonies grew on the surface of a 3,6 inch plate. After 4–6 weeks of incubation at 20° C. in the dark the orange colonies were visually selected (colonies containing more than 10 percent HDCO were supposed to be red) and were used for shake flask experiments. A 100 ml shake flask containing 25 ml synthetic medium was inoculated with a strain isolated as described above and incubated during 3 days (20° C., 250 rpm). Hereafter, 1 ml of the cell suspension was used to inoculate 100 ml synthetic medium in a 500 ml shake flask with baffle and incubation occured for 4 days at 20° C., 250 rpm. After this, the amount of astaxanthin, HDCO and dry weight were determined.

The amount of specific carotenoids was determined by suitable chromatographic techniques such as thin-layer chromatography, or HPLC.

To obtain strains with a higher astaxanthin content repeated mutagenization/selection steps are performed.

Although generally it was found that the relative amount of HDCO increased with an increasing amount of astaxanthin both in the literature and in our experiments, strains have now been found with a high astaxanthin content and with a low percentage of HDCO.

A high level of astaxanthin means that the amount is increased as compared with the wild type strain e.g. above about 650 µg/g dry weight (as shown in Johnson and Lewis. *J. Gen. Microbiol.* (1979) 115 178, Table 3). Preferably the amount is above 2000 µg/g dry weight, more preferably above 8000 µg/g dry weight.

The amount of HDCO which in the wild type strain is of the order of 0.5–1.0% relative to the amount of astaxanthin rapidly increases upon mutagenesis to levels of up to 35% relative to the astaxanthin level. A low percentage of HDCO is defined as lower than 10% HDCO, preferably less than 5% HDCO, more preferably less than 2% relative to astaxanthin or even lower than 1% HDCO whereby the astaxanthin is extracted from a strain containing an amount of astaxanthin higher than 650 µg/g dry weight.

The present invention provides strains which combine a high level of astaxanthin with a low percentage of HDCO. Preferred strains are those which have a level of astaxanthin above 1500 µg/g dry weight and a percentage of HDCO lower than 3% of the astaxanthin level.

To obtain Phaffia strains combining these characteristics it is possible to mutagenize a strain which has already been selected for high astaxanthin production, and an example of this is provided.

However, it is also possible to start with a wild type strain and first select for a decrease in the HDCO percentage and subsequently mutagenize for an increased level of astaxanthin (keeping the HDCO percentage low).

It is also possible to obtain strains having the desired characteristics of high astaxanthin production with low HDCO level, by using protoplast fusion. The combination of protoplasts obtained from cells with high HDCO and protoplasts obtained from cells with low HDCO level results in cells having the desired characteristics.

The astaxanthin isolated or contained in the cells can be formulated in animal feed or food. Use of this food or feed will give rise to the desired colour for example in salmonids, sea bream and eggs. The present invention thus provides an animal feed or food comprising yeast cells or yeast cell parts containing astaxanthin in an amount of at least 650 µg/g dry yeast weight and a 3-hydroxy-3',4'-didehydro-β,ψ-caroten-4-one concentration of less than 10% HDCO, preferably less than 5% HDCO, more preferably less than 2% HDCO or even lower than 1% HDCO relative to the astaxanthin level in the cells.

The method can also be employed to obtain strains having a low astaxanthin level and a low percentage of HDCO.

The following examples are only given to illustrate the invention and not to limit the invention in any way. It is immediately clear to a person skilled in the art that other mutagens and other Phaffia strains can be used to obtain the same or similar results.

Experimental

Media

Biomalt medium 122 gram MEX 11 (Diastatische Producten B.V. Leiden-Holland) was dissolved in 1 liter demineralized water, the pH was set at 6.4 and the solution was sterilized for 20 minutes at 120° C. For the preparation of Biomalt agar medium agar was added to a final concentration of 1.0% (w/v).

Potatodextrose (CM 11-2) agar medium

| | |
|---|---|
| Potatodextrose (Difco) | 39 g |
| demineralized water | 1000 ml |
| agar | 10 g |
| pH before autoclaving | 7.4 |

Sterilization is performed by heating for 20 minutes at 120° C.

Synthetic medium

| medium component | Concentration (g/l) |
|---|---|
| KH-phtalate | 20 |
| pH | 5.6 |
| NaCl | 0.06 |
| MgSO$_4$ | 0.88 |
| CaCl$_2$ | 0.20 |
| H$_2$SO$_4$ | 0.071 |
| NH$_4$Cl | 4.83 |
| KH$_2$PO$_4$ | 1 |
| citric acid | 0.015 |
| (NH$_4$)$_2$Fe (SO$_4$)$_2$ | 0.027 |
| ZnSO$_4$ | 0.005 |
| CuSO$_4$ | 0.0075 |
| MnSO$_4$ | 0.0006 |
| H$_3$BO$_3$ | 0.0006 |
| Na-molybdate | 0.0006 |
| KI | 0.00015 |
| Myo-inositol | 0.059 |
| nicotinic acid | 0.003 |
| Ca-D-panthotenate | 0.003 |
| vitamin B$_1$ | 0.003 |
| p-aminobenzoate | 0.002 |
| vitamin B$_6$ | 0.0003 |
| biotin | 0.00001 |
| glucose | 33 |

Sterilization was for 30 minutes at 110° C.

Maintenance of cultures

Cultures of *Phaffia rhodozyma* are stored in two ways:
a. Slants containing biomalt agar medium were prepared from *Phaffia rhodozyma* CBS 6938 and the mutants derived thereof. These slants are incubated 1 week at 20° C. and subsequently frozen at −20° C.
b. Vials are prepared from cultures which are grown in 100 ml shake flasks (with baffle) containing 25 ml synthetic medium (20° C., 250 rpm). Cultures are centrifuged and suspended in demineralized water (filtered in a milli q filter system from Millipore). containing 10% (v/v) glycerol, the vials are frozen in liquid nitrogen and stored at −80° C.

High Performance Liquid Chromatography

Extraction procedure

A sample of 2.5 g culture was pipetted into a closable 15 ml glass centrifuge tube and centrifuged (3200× g, 25 minutes, 15° C.). The supernatant was removed. 1.5 ml cold aceton (5° C.) and 5 g glass beads (3 mm diameter) were added and mixed by a vortex. The centrifuge tubes were mixed on a Vibrax™ mixer (IKA Model Vibrax VXR) and the mixer was set at maximal speed during 60 minutes.

Hereafter, acetone (20° C.) was added to a final suspension volume of 10 ml (without the glass beads). The suspension was homogenized and centrifuged (3200× g, 5 minutes, 20° C.). The supernatant was used for HPLC analysis.

Equipment

Columns: Novapack™ C 18 Catridge (5×100 mm) (Waters Associates, Milford, Massachusetts)

Detector: Waters 486 Tunable Absorbance Detector

Control and

Integration: Integration was performed with software "Maxima package" commercially available from Waters Instruments.

Autosampler: Waters 712 Wisp with cool system.

Solvents

Bisethyl hexylphosphate (16 g/l) and formic acid (40 ml/l) in acetonitril.

The solvents were HPLC grade.

Operation

Flow: 1 ml/min.

Detector: 471 nm

Temperature: 18° C.

Injection volume: 20 µl

Astaxanthin standard

A purified astaxanthin preparation (Gist-brocades, R&D department CMA, Delft, The Netherlands) was used as a standard. Briefly, purification was performed as follows; Astaxanthin in Phaffia-oil (Aquaculture 20 123–134 (1980)), is treated with hexane. After filtration and washing the crystalline product is dissolved in methylene chloride (MTC), methanol is added (in a ratio of 4:3 with respect to MTC) and the mixture is concentrated under vacuum. The crude astaxanthin obtained is dissolved in chloroform and chromatographed over silica gel (with toluene/acetone 4:1). The dried product is again crystallized from a mixture of MTC and methanol, optionally this is repeated several times. As far as possible the procedure is performed protected from light. Further characterization of the product is by HPLC.

The astaxanthin content was expressed as mg astaxanthin/kg broth. The amount of 3-hydroxy-3',4'-didehydro-$\beta,\psi$-caroten-4-one was calculated in the same way as astaxanthin. During the calculations it was assumed that astaxanthin has the same extinction coefficient as 3-hydroxy -3',4'-didehydro-$\beta,\psi$-caroten-4-one and therefore the same astaxanthin standard sample was used for the calculations. The amount of 3-hydroxy-3',4'-didehydro-$\beta,\psi$-caroten-4-one was expressed in mg 3-hydroxy-3',4'-didehydro-$\beta,\psi$-caroten-4-one/kg broth.

Dry weight measurement

Plastic 12 ml centrifuge tubes (Greiner) were dried in an incubator for 24 hours (105° C.). The tubes were cooled down in an excicator over dry silicagel and thereafter the weight (A) was determined in four decimals on a Mettler AE200 balance. The centrifuge tubes were filled with about 10 ml cell suspension and the weight (B) was determined as described above. The cell suspensions were centrifuged at room temperature (10 minutes, 4000 rpm) and the supernatant was decanted. The centrifuge tubes plus pellets were dried in an incubator (24 hours, 105° C.). Afterwards the tubes were cooled down in the excicator and the weight was measured as described above (C).

All dry weight measurements were performed in duplo.

Calculation: dry weight (g/kg)={(C−A)/(B−A)}*1000 and A,B,C were expressed in grams.

Chemicals

The standard samples of astaxanthin needed for the HPLC measurements were prepared at Gist-brocades (CMA department). All other chemicals used in these experiments are commercially available and of analytical grade.

Mutagenesis

Strain improvement was achieved by classical mutation. Mutations were induced by the use of NTG (N-methyl-N'-nitro-N-nitrosoguanine), EMS (ethylmethanesulphonate) or ultraviolet irradiation and a survival value of 10% was considered to induce sufficient mutations. Appropriate dilutions of cell-suspensions were made on agar plates and after incubation the colour intensity of the red colonies were compared by eye and the colonies showing the highest red colour intensity were isolated and used for shake flask experiments.

EXAMPLE 1

A strain of *Phaffia rhodozyma* with high astaxanthin and high 3-hydroxy-3',4'-didehydro-$\beta,\psi$-caroten-4-one content, *Phaffia rhodozyma* PF 11–3, was obtained through repeated rounds of mutagenesis and selection. This strain was used to isolate strains with low 3-hydroxy-3',4'-didehydro-$\beta,\psi$-caroten-4-one content. A 100 ml culture was grown on biomalt medium in a 500 ml flask (with baffle) for 72 hours in a shaking incubator (250 rpm, 20° C.) The culture was centrifuged (4000 rpm, 10 minutes) and suspended in 9 ml Tris-buffer (100 mM, pH 8.0). The cell-density of the suspension was set at $10^8$/ml. Subsequently, 1 ml 10 mM NTG in 100 mM Na-acetate buffer pH 4.3 was added to 10 ml of the cell suspension. At appropriate time intervals samples were drawn and a part of the sample was diluted in physiological salts medium and plated out on potato-dextrose agar for a survival test. Another part of the sample was frozen in 10% glycerol. After determination of the 10% survival the involved sample was plated out on potato-dextrose agar and incubated one week at 20° C. Colonies with the most intensive red colour were selected by eye and tested in a 100 ml shake flask (with baffle) containing 25 ml synthetic medium (250 rpm, 20° C.). After 72 hours 1 ml of this culture was used to inoculate 100 ml of the same medium in a 500 ml shake flask (with baffle) and incubated under the same conditions as is described for the preculture. After 98 hours 2.5 g culture was used to prepare a sample for HPLC and 10 ml was used for a dry weight measurement. Strain PF 11–12 was selected after mutagenesis of the parent strain PF 11–3 and the astaxanthin and 3-hydroxy-3',4'-didehydro-$\beta,\psi$-caroten-4-one content was estimated by HPLC. In Table 1 the values of astaxanthin and 3-hydroxy-3',4'-didehydro-$\beta,\psi$-caroten-4-one content of these strains are presented and compared with the wild type strain *Phaffia rhodozyma* CBS 6938.

TABLE 1

| Strain | Astaxanthin content (μg/g DWT) | 3-hydroxy-3',4'-didehydroxy-β,ψ-caroten-4-one ratio* |
|---|---|---|
| Phaffia rhodozyma CBS 6938 | 220 | 0.20 |
| Phaffia rhodozyma PF 11-3 | 1280 | 0.22 |
| Phaffia rhodozyma PF 11-12 | 1670 | 0.02 |
| Phaffia rhodozyma CBS 215.88 | n.d. | 0.17 |
| Phaffia rhodozyma CBS 224.87 | n.d. | 0.37 |
| Phaffia rhodozyma CBS 225.87 | n.d. | 0.16 |

The Phaffia rhodozyma strain CBS 215.88, CBS 224.87 and CBS 225.87 and the method by which they have been obtained is described in WO 88/08025. Briefly, Phaffia rhodozyma ATCC 24261 was mutagenized with EMS to obtain strain CBS 224.87. Strain CBS 224.87 was subsequently mutagenized with NTG to obtain CBS 225.87. Finally, strain CBS 215.88 is a reisolate from strain CBS 225.87. It is observed that these mutant strains contain a relatively high level of HDCO.

It is noted that when the mutant strain PF 11-12 is compared with the parent strain PF 11-3, PF 11-12 contains an increased amount of astaxanthin while the 3-hydroxy-3',4'-didehydro-β,ψ-caroten-4-one content decreased a factor 10. PF 11-12 was deposited at Centraal Bureau voor Schimmelcultures (Baarn, The Netherlands) on 16 December 1991 under number CBS 797.91.

EXAMPLE 2

A culture of Phaffia rhodozyma PF 11-12 was treated as described in Example 1, with the alteration that 0.4 ml EMS (Merck) was used as a mutagen instead of 1 ml 10 mM NTG. The selection was carried out as described in Example 1. Strain PF 11-18 was selected from the parent strain PF 11-12 and in Table 2 the values of astaxanthin and 3-hydroxy-3',4'-didehydro-β,ψ-caroten-4-one contents are presented:

TABLE 2

| Strain | Astaxanthin content (μg/g DWT) | 3-hydroxy-3',4'-didehydro-β,ψ-caroten-4-one ratio* |
|---|---|---|
| Phaffia rhodozyma CBS 6938 | 220 | 0.20 |
| Phaffia rhodozyma PF 11-12 | 1670 | 0.02 |
| Phaffia rhodozyma PF 11-18 | 1800 | 0.03 |

*as in Table 1

In this example it is shown that mutants with higher astaxanthin content can be isolated from parent strains containing low 3-hydroxy-3',4'-didehydro-β,ψ-caroten-4-one (PF 11-12), while the 3-hydroxy-3',4'-didehydro-β,ψ-caroten -4-one content of the mutant strain (PF 11-18) remains low.

EXAMPLE 3

A culture of Phaffia rhodozyma PF 11-18 was treated as described in Example 1 and 1 ml 10 mM NTG was used. The selection was carried out as described in Example 1. Strain PF 11-30 was selected from the parent strain PF 11-18. In Table 3 the values of astaxanthin and 3-hydroxy-3',4'-didehydro-β,ψ-caroten-4-one contents are presented:

TABLE 3

| Strain | Astaxanthin content (μg/g DWT) | 3-hydroxy-3',4'-didehydro-β,ψ-caroten-4-one ratio* |
|---|---|---|
| Phaffia rhodozyma CBS 6938 | 220 | 0.20 |
| Phaffia rhodozyma PF 11-18 | 1800 | 0.03 |
| Phaffia rhodozyma PF 11-30 | 1960 | 0.02 |

*as in Table 1

In this example it is shown that mutants with higher astaxanthin content can be isolated from parent strains containing low 3-hydroxy-3',4'-didehydro-β,ψ-caroten-4-one (PF 11-18), while the 3-hydroxy-3',4'-didehydro-β,ψ-caroten -4-one content of the mutant strain (PF 11-30) remains low.

EXAMPLE 4

A strain of Phaffia rhodozyma, namely PF 11-36 obtained after mutagenesis of strain PF 11-12, containing a high level 3-hydroxy-3',4'-didehydro-β,ψ-caroten-4-one content relative to astaxanthin, was used to isolate strains with a low 3-hydroxy-3',4'-didehydro-β,ψ-caroten-4-one content ratio. A 100 ml culture was grown on synthetic medium in a 500 ml flask (with baffle) for 65 hours in a shaking incubator (250 rpm, 20° C.). The culture was centrifuged (4000 rpm, 10 minutes) and suspended in 25 ml Tris buffer (100 mM, pH 7.5). The cell density of the suspension was set at $10^8$/ml. Subsequently, 1 ml 10 mM NTG in 100 mM acetate buffer pH 4.3 was added to 10 ml of the cell suspension. At appropiate time intervals samples were drawn and were diluted into 0.1 M Tris buffer pH 7.5. The cells were washed three times in physiological salts medium and plated out on biomalt agar medium to estimate the survival. A part of the dilution was frozen in 10% glycerol (−80° C.). After determination of the sample containing 10% survival, appropriate dilutions of the frozen sample were plated out on the synthetic medium agar (100–500) colonies/3,6 inch plate). After 4–6 weeks incubation (20° C.) the orange coloured colonies were visually selected and tested in shake flask experiments as described above. In table 4 the astaxanthin contents and 3-hydroxy-3',4'-didehydro-β,ψ-caroten-4-one ratio's of the various isolated strains of Phaffia rhodozyma PF 11-36 are presented.

These results show clearly that by selection on colour, mutants can be selected with astaxanthin levels comperable with that of the parent strain. These strains contain high levels of astaxanthin but the 3-hydroxy-3',4'-didehydro-β, ψ-caroten-4-one ration has been strongly reduced in relation to the amount of astaxanthin.

TABLE 4

Astaxanthine contents and 3-hydroxy-3',4'-didehydro-
β,ψ-caroten-4-one ratio's of the various isolated strains of
Phaffia rhodozyma PF 11-36.

| Strain | Astaxanthine content (µg/g DWT) | 3-hydroxy-3',4'--didehydro-β,-caroten-4-one ratio* |
|---|---|---|
| Phaffia rhodozyma PF 11-36 | 2303 | 0.14 |
| Phaffia rhodozyma PF 11-36-13 | 1545 | 0.05 |
| Phaffia rhodozyma PF 11-36-15 | 542 | 0.05 |
| Phaffia rhodozyma PF 11-36-17 | 1104 | 0.07 |
| Phaffia rhodozyma PF 11-36-27 | 916 | 0.08 |
| Phaffia rhodozyma PF 11-36-47 | 643 | 0.06 |
| Phaffia rhodozyma PF 11-36-113 | 852 | 0.05 |
| Phaffia rhodozyma PF 11-36-123 | 899 | 0.07 |
| Phaffia rhodozyma PF 11-36-240 | 1795 | 0.07 |
| Phaffia rhodozyma PF 11-36-263 | 521 | 0.06 |
| Phaffia rhodozyma PF 11-36-422 | 1200 | 0.09 |
| Phaffia rhodozyma PF 11-36-489 | 2205 | 0.02 |
| Phaffia rhodozyma PF 11-36-500 | 2180 | 0.07 |
| Phaffia rhodozyma PF 11-36-653 | 931 | 0.04 |
| Phaffia rhodozyma PF 11-36-672 | 970 | 0.03 |
| Phaffia rhodozyma PF 11-36-678 | 1580 | 0.01 |
| Phaffia rhodozyma PF 11-36-696 | 1408 | 0.03 |

*the 3-hydroxy-3',4'-didehydro-β,ψ-caroten-4-one ratio is defined as the ratio of 3-hydroxy-3',4'-didehydro-β,ψ-caroten-4-one content and astaxanthin content plus the 3-hydroxy-3',4'-didehydro-β,ψ-caroten-4-one content.

We claim:

1. A *Phaffia rhodozyma* strain having an intracellular concentration of more than 650 µg astaxanthin per g dry weight and a 3-hydroxy-3',4'-didehydro-β,ψ-caroten-4-one (HDCO) percentage relative to the amount of astaxanthin of less than 5% by weight.

2. The *P. rhodozyma* strain of claim 1 which has an intracellular astaxanthin concentration of more than 1,500 µg/g of dry weight.

3. The *P. rhodozyma* strain of claim 2 which has an intracellular astaxanthin concentration of more than 2000 µg per g of dry weight.

4. The *P. rhodozyma* strain of claim 1 wherein the percentage of HDCO relative to astaxanthin is less than 2% by weight.

5. The *P. rhodozyma* strain of claim 4 wherein the percentage of HDCO relative to astaxanthin is less than 1% by weight.

6. The *P. rhodozyma* strain of claim 1 which has an intracellular astaxanthin content of more than 1500 µg/g dry weight and a percentage of HDCO less than 3% of astaxanthin by weight.

7. The *P. rhodozyma* strain of claim 6 in which the percentage of HDCO is less than 1% of astaxanthin by weight.

8. A method for modifying the relative astaxanthin and HDCO levels of a *Phaffia rhodozyma* strain, which method comprises:

culturing a *Phaffia rhodozyma* strain having an astaxanthin content of more than 650 µg per g dry weight and a level of 3-hydroxy-3',4'-didehydro-β,ψ-caroten-4-one (HDCO) of greater than 5% by weight relative to the amount of astaxanthin, mutating the *Phaffia rhodozyma* strain, visually selecting colonies having a relatively more intense orange color than the other colonies, growing the selected orange colonies on a fluid medium, extracting the carotenoids from the cells of said colonies, determining the amounts of astaxanthin and HDCO in the carotenoid extracts, and selecting a strain having an astaxanthin content of more than 650 µg per g dry weight and a level of 3-hydroxy-3',4'-didehydro-β,ψ-caroten-4-one (HDCO) of less than 5% by weight relative to the amount of astaxanthin.

9. A method for modifying the astaxanthin and HDCO levels of a *Phaffia rhodozyma* strain, which method comprises:

culturing a parent *Phaffia rhodozyma* strain having an astaxanthin content of more than 650 µg per g dry weight and a level of 3-hydroxy-3',4'-didehydro-β,ψ-caroten-4-one (HDCO) of greater than 5% by weight relative to the amount of astaxanthin, mutating the *Phaffia rhodozyma* strain, visually selecting colonies having a relatively more intense orange color than the other colonies, growing the selected orange colonies on a fluid medium, extracting the carotenoids from the cells of said colonies, determining the amounts of astaxanthin and HDCO in the carotenoid extracts, and selecting a strain having an astaxanthin content less than that of the parent strain and a level of HDCO of less than 5% by weight relative to the amount of astaxanthin.

* * * * *